US012750589B2

(12) United States Patent
Viering

(10) Patent No.: US 12,750,589 B2
(45) Date of Patent: Sep. 29, 2026

(54) MEDICAL IMAGING SYSTEMS AND METHODS FOR AUTOMATIC BRIGHTNESS CONTROL BASED ON REGION OF INTEREST

(71) Applicant: Boston Scientific Scimed, Inc., Maple Grove, MN (US)

(72) Inventor: Kirsten Viering, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/928,471

(22) Filed: Oct. 28, 2024

(65) Prior Publication Data

US 2025/0150716 A1 May 8, 2025

Related U.S. Application Data

(60) Provisional application No. 63/595,389, filed on Nov. 2, 2023.

(51) Int. Cl.
*H04N 23/76* (2023.01)
*A61B 1/00* (2006.01)
(Continued)

(52) U.S. Cl.
CPC ......... *H04N 23/72* (2023.01); *A61B 1/00006* (2013.01); *A61B 1/00045* (2013.01);
(Continued)

(58) Field of Classification Search
CPC ........ H04N 23/56; H04N 23/71; H04N 23/72; H04N 23/73; H04N 23/74; H04N 23/76;
(Continued)

(56) References Cited

U.S. PATENT DOCUMENTS

| | | | | |
|---|---|---|---|---|
| 2011/0069762 | A1 | 3/2011 | Yoshino et al. | |
| 2013/0239063 | A1 * | 9/2013 | Ubillos ................ | G06F 3/0485 715/838 |

(Continued)

FOREIGN PATENT DOCUMENTS

| | | | |
|---|---|---|---|
| CN | 114359063 | A | 4/2022 |
| CN | 116888970 | A | 10/2023 |
| WO | 2015106955 | A1 | 7/2015 |

OTHER PUBLICATIONS

Mathialagan Prabhakaran et al: "Computer Vision Techniques for Upper Aero-Digestive Tract Tumor Grading Classification—Addressing Pathological Challenges," Pattern Recognition Letters, vol. 144, Jan. 16, 2021 (Jan. 16, 2021), pp. 42-53, XP086504397, Elsevier, Amsterdam, NL, ISSN: 0167-08655, DOI: 10.1016/J. Patrec.2021.01.002 [retrieved on Jan. 16, 2021].

*Primary Examiner* — Hung Q Dang
*Assistant Examiner* — Jose M Mesa
(74) *Attorney, Agent, or Firm* — Bookoff McAndrews, PLLC

(57) ABSTRACT

A method for performing automatic brightness control may include receiving an image of a target site from an imaging system of a medical device, and identifying a region of interest in the image. The region of interest may include a physical feature in the target site identified in the image. The method may further include determining a current image brightness value for the identified region of interest, and adjusting one or more operating parameters of the imaging system based on the current image brightness value and a target image brightness value.

16 Claims, 8 Drawing Sheets

(51) Int. Cl.

| | |
|---|---|
| ***G06T 11/10*** | (2026.01) |
| ***G06V 10/25*** | (2022.01) |
| ***G06V 10/44*** | (2022.01) |
| ***G06V 10/50*** | (2022.01) |
| ***G06V 10/56*** | (2022.01) |
| ***G06V 10/60*** | (2022.01) |
| ***H04N 23/50*** | (2023.01) |
| ***H04N 23/56*** | (2023.01) |
| ***H04N 23/611*** | (2023.01) |
| ***H04N 23/71*** | (2023.01) |
| ***H04N 23/72*** | (2023.01) |
| ***H04N 23/73*** | (2023.01) |
| ***H04N 23/74*** | (2023.01) |

(52) U.S. Cl.

CPC .............. *G06T 11/10* (2026.01); *G06V 10/25* (2022.01); *G06V 10/44* (2022.01); *G06V 10/50* (2022.01); *G06V 10/56* (2022.01); *G06V 10/60* (2022.01); *H04N 23/555* (2023.01); *H04N 23/56* (2023.01); *H04N 23/611* (2023.01); *H04N 23/71* (2023.01); *H04N 23/73* (2023.01); *H04N 23/74* (2023.01); *H04N 23/76* (2023.01); *G06T 2210/41* (2013.01); *G06V 2201/03* (2022.01)

(58) Field of Classification Search

CPC .... H04N 23/555; H04N 23/611; G06V 10/25; G06V 10/44; G06V 10/50; G06V 10/56; G06V 10/60; G06V 2201/03; A61B 1/00006; A61B 1/00045; G06T 11/001; G06T 2210/41

See application file for complete search history.

(56) References Cited

U.S. PATENT DOCUMENTS

| | | | | |
|---|---|---|---|---|
| 2019/0075230 | A1* | 3/2019 | Takeda ................. | H04N 23/631 |
| 2019/0090826 | A1* | 3/2019 | Carmi .................. | A61B 6/5217 |
| 2023/0168392 | A1 | 6/2023 | Ezure | |
| 2024/0016387 | A1* | 1/2024 | Strasfeld ............... | G06T 7/0012 |

* cited by examiner

MEDICAL IMAGING SYSTEMS AND METHODS FOR AUTOMATIC BRIGHTNESS CONTROL BASED ON REGION OF INTEREST

CROSS-REFERENCE TO RELATED APPLICATIONS

This application claims the benefit of priority of U.S. Provisional Patent Application No. 63/595,389, filed Nov. 2, 2023, the entirety of which is incorporated herein by reference.

TECHNICAL FIELD

The disclosure relates generally to systems and methods for automatic brightness control. More specifically, aspects of the disclosure pertain to systems and methods for identifying one or more regions of interest in an image and performing automatic brightness control based on the identified region(s) of interest.

BACKGROUND

A medical imaging system may include an imaging device and a light source integrated with a medical device, such as an endoscope. The endoscope may be inserted into and navigated through a body lumen of a patient to a target site during a medical procedure. The light source may be configured to emit light onto the target site to illuminate objects and/or features within the target site to facilitate a visualization thereof in images captured by the imaging device. In some examples, the medical imaging system may be configured to perform automatic brightness control to evaluate and adjust, if needed, one or more parameters of the imaging system and/or perform additional image processing to optimize a brightness or illumination of the target site in subsequent images captured by the imaging device.

SUMMARY

Aspects of techniques described herein relate to methods for performing automatic brightness control. An example method may include receiving an image of a target site from an imaging system of a medical device, and identifying a region of interest in the image. The region of interest may include a physical feature in the target site identified in the image. The method may also include determining a current image brightness value for the identified region of interest, and adjusting one or more operating parameters of the imaging system based on the current image brightness value and a target image brightness value.

In any of the example methods disclosed herein, the method may include determining an average pixel intensity value for a subset of pixels of the image including the region of interest. The average pixel intensity value may be the current image brightness value. In some examples, identifying the region of interest in the image includes detecting a plurality of edges in the image, and identifying, as the region of interest, a subset of pixels, among a plurality of subsets of pixels in the image, having a highest edge density. The subset of pixels may include the physical feature. The image may be converted to grayscale prior to detecting the plurality of edges.

In other examples, the image is in a first color space, and identifying the region of interest in the image may include converting the image from the first color space to a second color space, generating a plurality of histograms for the image in the second color space, executing a color selection process based on an analysis of one or more of the plurality of histograms, and identifying the region of interest based on the color selection process. The second color space may include a plurality of channels, and generating the plurality of histograms may include generating a histogram for each of the plurality of channels, where the one or more of the plurality of histograms analyzed represent color distributions in the image.

In some aspects, the analysis of the one or more of the plurality of histograms may include identifying color shade differentiations in the image, and determining a suspicious color area in the image based on a deviation of the identified color shade differentiations from a pattern of color shade differentiations for a type of anatomy included in the image. A subset of pixels in the image including the suspicious color area may be identified as the region of interest, and the subset of pixels may include the physical feature. In some examples, determining the suspicious color area may include comparing the one or more of the plurality of histograms to one or more reference patterns of color shade differentiations for the type of anatomy to identify the deviation. In other examples, determining the suspicious color area may include providing the one or more of the plurality of histograms as input to a machine learning model trained to identify the deviation from one or more learned patterns of color shade differentiations for the type of anatomy.

In some aspects, executing the color selection process based on the analysis of the one or more of the plurality of histograms may include applying a mask to each pixel in the image that is not included in the suspicious color area to generate a masked image. Additionally, a binary image may be generated based on the masked image to facilitate the identifying of the region of interest.

In further examples, identifying the region of interest in the image may include receiving a feature type associated with the physical feature to be identified in the image, and based on the feature type, detecting the physical feature corresponding to the feature type in the image. A subset of pixels in the image including the detected physical feature may be identified as the region of interest. The feature type may be a shape or a pattern associated with the physical feature.

In some aspects, the imaging system includes a light source configured to illuminate the target site, and adjusting the one or more operating parameters of the imaging system may include adjusting an intensity of light emitted by the light source to illuminate the target site. The intensity of light may be adjusted by controlling an amount of current supplied to the light source. In other aspects, the imaging system includes an imaging device configured to capture the image, and adjusting the one or more operating parameters of the imaging system may include adjusting one or more of a gain or an exposure time of the imaging device.

Additionally, the techniques described herein relate to a computing system for performing automatic brightness control, the computing system including at least one memory storing instructions, and at least one processor coupled to the at least one memory and configured to execute the instructions to perform operations. The operations may include receiving, from a medical imaging system including an imaging device and a light source, an image of a target site captured by the imaging device as the light source is illuminating the target site. The image may include a plurality of pixels. The operations may also include identifying a subset of the plurality of pixels as a region of interest in the image. The subset of the plurality of pixels may include a physical feature in the target site detected in the image. The operations may further include determining a current image brightness value based on an average pixel intensity value for the subset of the plurality of pixels, and based on the current image brightness value, adjusting one or more operating parameters of one or more of the light source or the imaging device to achieve a target image brightness value for the subset of the plurality of pixels identified as the region of interest.

In any of the exemplary computing systems disclosed herein, identifying the subset of the plurality of pixels as the region of interest in the image may include detecting a plurality of edges in the image, and identifying a subset of the plurality of pixels, from a plurality of subsets of the plurality of pixels in the image, having a highest edge density as the region of interest.

In other examples, the image may be in a first color space, and identifying the subset of the plurality of pixels as the region of interest in the image may include converting the image from the first color space to a second color space, generating a plurality of histograms for the image in the second color space, identifying color shade differentiations in the image based on an analysis of the one or more of the plurality of histograms, and determining a suspicious color area in the image based on a deviation of the identified color shade differentiations from a pattern of color shade differentiations for a type of anatomy at the target site. A subset of the plurality of pixels in the image including the suspicious color area may be identified as the region of interest.

In further examples, identifying the subset of the plurality of pixels as the region of interest in the image may include receiving a feature type associated with the physical feature to be detected in the image, and based on the feature type, detecting the physical feature corresponding to the feature type in the image. A subset of pixels in the image including the detected physical feature may be identified as the region of interest.

Other aspects of techniques described herein may relate to a medical imaging system. An example medical imaging system may include a medical device including an imaging device configured to capture an image of a target site and a light source configured to illuminate the target site as the image is captured. The medical imaging system may also include a computing device communicatively coupled to the medical device. The computing device may include at least one memory storing instructions, and at least one processor coupled to the at least one memory and configured to execute the instructions to perform operations. The operations may include receiving the image from the medical device, and identifying a region of interest in the image including a physical feature in the target site detected in the image. The region of interest may be identified using at least one of edge detection, color detection, or feature detection to detect the physical feature. The operations may further include determining a current image brightness value for the identified region of interest, and adjusting one or more operating parameters of one or more of the light source or the imaging device based on the current target image brightness value and a target brightness value for the identified region of interest to optimize a brightness of the region of interest in subsequent images of the target site captured by the imaging device.

It may be understood that both the foregoing general description and the following detailed description are exemplary and explanatory only and are not restrictive of the invention, as claimed. As used herein, the terms "comprises," "comprising," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator/toward a treatment site, and the term "proximal" refers to a direction toward an operator. The term "approximately," or like terms (e.g., "substantially"), includes values +/−10% of a stated value.

BRIEF DESCRIPTION OF THE DRAWINGS

The accompanying drawings, which are incorporated in and constitute a part of this specification, illustrate examples of this disclosure and, together with the description, serve to explain the principles of the disclosure.

DETAILED DESCRIPTION

Figure 1:
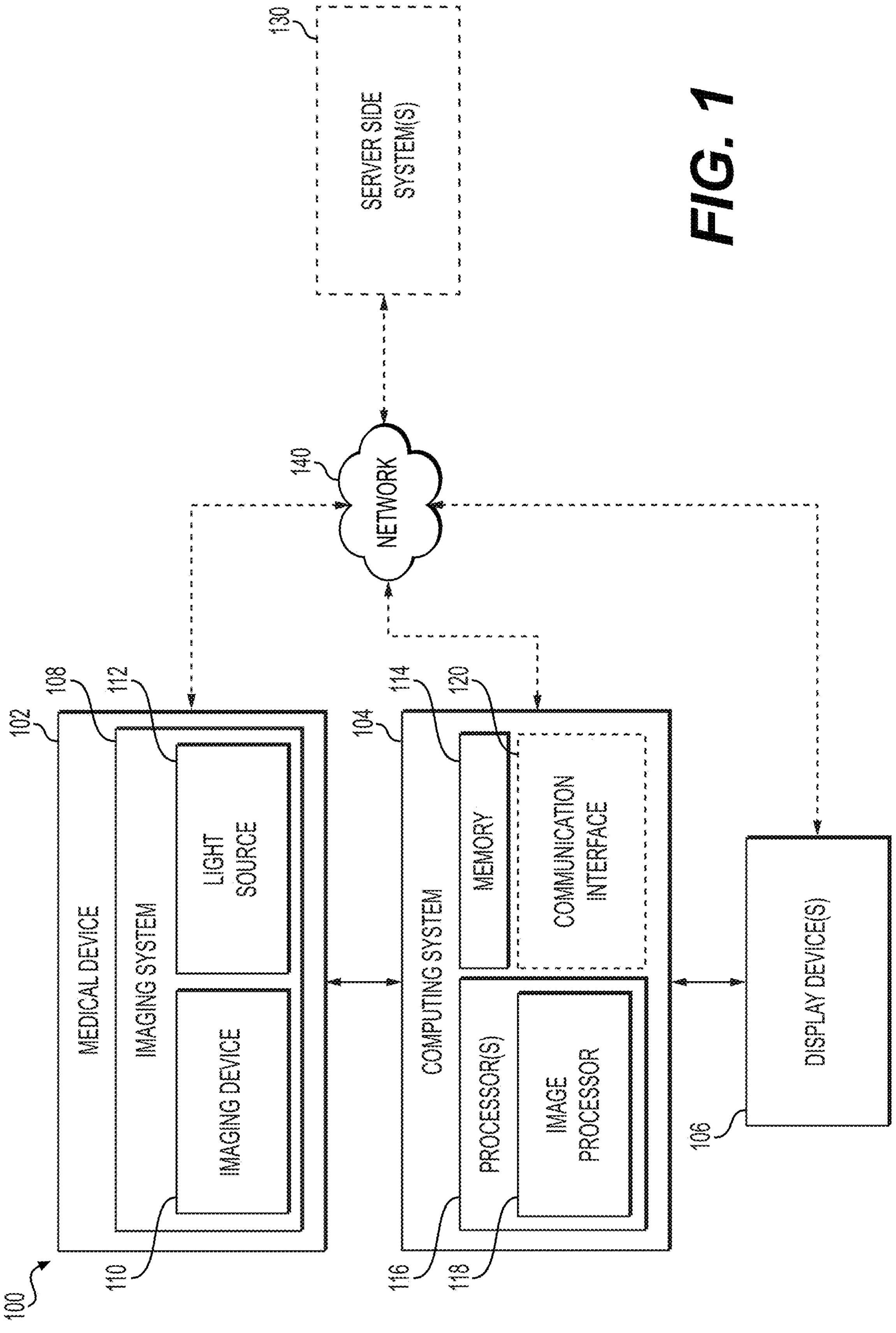
FIG. 1 depicts an example environment in which automatic brightness control processes may be performed.

As briefly mentioned above, a medical imaging system may include a light source configured to emit light onto a target site during a medical procedure to illuminate physical objects and/or features within the target site to facilitate visualization of the physical objects and/or features in images of the target site captured by an imaging device of the system. In some examples, the medical imaging system may be configured to perform automatic brightness control to evaluate and adjust, if needed, one or more operating parameters of the medical imaging system and/or perform additional image processing to optimize a brightness or illumination of subsequent images captured by the imaging device.

Some conventional systems and methods for performing automatic brightness control may evaluate brightness across an entirety of the image, and, based on the evaluation, adjust the one or more operating parameters of the medical imaging system to optimize a brightness or illumination of the image as a whole. For example, the image may include a plurality of pixels. As part of the evaluation, a plurality of pixel intensity values for the plurality of pixels may be averaged to determine a target image brightness value for use in the adjustment. However, a region of interest, including one or more objects and/or features of interest for visualization, is often located in only a subset or portion of the image. Therefore, adjustments made to optimize a brightness or illumination of the image as a whole may not necessarily result in an optimal brightness or illumination of the region of interest.

Other conventional systems and methods for performing automatic brightness control may evaluate brightness in a center region of the image, and based on the evaluation, adjust the one or more operating parameters of the medical imaging system to optimize a brightness or illumination of the center region of the image. For example, as part of the evaluation, pixel intensity values for a subset of the pixels forming the center region of the image may be averaged, and the adjustment may be based on the average pixel intensity value for the center region. The center region may be evaluated based on an assumption that the center region is most likely to include objects and/or features of interest for visualization. However, oftentimes objects and/or features of interest may not be located at or may extend beyond a center region of the image. Additionally, based on anatomical configurations, an operator of the endoscope may be unable to navigate the medical device in a manner that would enable the objects and/or features of interest to be positioned in the center region.

Further conventional systems and methods for performing automatic brightness control may adjust the one or more operating parameters of the medical imaging system to reduce or eliminate hot spots. Hot spots may be comprised of saturated pixels (e.g., white pixels) that cause details of any objects and/or features at the locations of the saturated pixels to become washed out or unable to be visualized. To reduce or eliminate the hot spots, an exemplary automatic brightness control process may determine a percentage or ratio of saturated pixels, and adjust the one or more operating parameters of the medical imaging system until the percentage or ratio of saturated pixels falls below a threshold. Although such adjustment may reduce or eliminate hotspots, the adjustment may also cause remaining portions of the image to become darker, which may ultimately impact the operator's ability to visualize objects and/or features of interest when they are located in the now darker portions of the image.

Therefore, aspects of this disclosure are directed to system and methods for performing automatic brightness control based on or specific to a region of interest identified in an image captured by the medical imaging system. The disclosed aspects improve the field of medical image processing including, for example, the field of automatic image brightening control. The identified region of interest may be a region of the image including the physical objects and/or features of interest in a target site for visualization. A variety of different techniques, including but not limited to, edge detection, color detection, and/or feature detection techniques, may be applied to identify the region of interest in the image. The automatic brightness control may then be performed to achieve a target image brightness value for optimal (or otherwise improved) visualization within the identified region of interest. For example, a current image brightness value for the region of interest may be determined based on an average of pixel intensity values for a subset of pixels in the image comprising the identified region of interest. One or more operating parameters of the medical imaging system may then be adjusted based on the current image brightness value and the target brightness value. For example, a difference between the current image brightness value and the target brightness value may be determined and utilized to adjust the one or more operating parameters such that the target brightness value for the region of interest can be achieved. Such adjustment may optimize a brightness or illumination of the physical objects and/or features of interest within the region of interest in subsequent images of the target site by, for example, optimizing raw image data captured by the imaging device. In some examples, additional image processing techniques may be performed on the raw image data received to further enhance the brightness or illumination beyond what was achievable through the adjustment of the imaging system operating parameters. As compared with conventional technologies, the disclosed aspects improve visualization of regions of interest in the target site.

FIG. 1 depicts an exemplary environment 100 in which automatic brightness control processes may be implemented. Environment 100 may include one or more of a medical device 102, a computing system 104, one or more display device(s) 106, one or more optional server side system(s) 130, and/or a network 140.

Medical device 102 may be used to perform a diagnostic and/or interventional medical procedure on a patient, hereinafter referred to as a medical procedure for brevity. Medical device 102 may be an endoscope or other type of scope, such as a bronchoscope, ureteroscope, duodenoscope, gastroscope, endoscopic ultrasonography ("EUS") scope, colonoscope, laparoscope, arthroscope, cystoscope, aspiration scope, sheath, or catheter, among other examples.

Medical device 102 may include an imaging system 108. Imaging system 108 may include at least one imaging device 110 and at least one light source 112. Imaging device 110 may be located at a distal end of medical device 102 (e.g., at a distal tip of medical device 102). Imaging device 110 may be configured to continuously capture image signals as the distal end of medical device 102 is inserted into and navigated through a body lumen of the patient to a target site during the medical procedure. Imaging device 110 may include one or more cameras, one or more image sensors, one or more endoscopic viewing elements, or one or more optical assemblies including one or more image sensors and one or more lenses, among other similar devices. In some examples, light source 112 may be located at the distal end of medical device 102 (e.g., at the distal tip of medical device 102) along with imaging device 110. In other examples (not shown), light source 112 may be a separate device or may be integrated with computing system 104, with light from light source 112 being transmitted via fibers extending a length of medical device 102 (e.g., from a proximal end of medical device 102 connected to computing system 104 to the distal tip of medical device 102). Light source 112 may be configured to illuminate areas of the patient's body (e.g., the target site) during the medical procedure to facilitate imaging of the target site by imaging device 110. Light source 112 may include one or more LEDs, incandescent light sources, optical fibers, and/or other illuminators.

One or more components of medical device 102, including imaging system 108 and the components thereof, may be communicatively coupled to computing system 104 via wired connections and/or wireless connections (e.g., over network 140) to enable communication of various signals between medical device 102 and computing system 104. For example, image signals captured by imaging device 110 (e.g., raw image data) may be received by computing system 104. Additionally, computing system 104 may provide one or more signals to the imaging device 110 and/or light source 112 to cause one or more parameters of imaging device 110 and/or light source 112, respectively, to be adjusted, as described in detail below.

In some examples, computing system 104 is a controller, a control unit, a computing device, or other similar standalone processing unit separate from medical device 102. In other examples, computing system 104 may be integrated with medical device 102. For example, computing system 104 may be positioned in a handle of medical device 102. In other examples, computing system 104 may be positioned at the distal end of medical device 102.

Computing system 104 may include a memory 114 and one or more processor(s) 116. Memory 114 may store instructions to be executed by processor(s) 116 to cause computing system 104 to perform corresponding operations. At least a portion of the instructions stored in memory 114 may include an automatic brightness control process. Memory 114 may also include one or more data stores. Additionally or alternatively, computing system 104 may include one or more data stores separate from memory 114. Processor(s) 116 may include at least one image processor 118. Image processor 118 may be configured to process one or more image signals (e.g., raw image data) captured by imaging device 110 and received by computing system 104 to generate an image. Additionally, image processor 118 may be configured to apply the automatic brightness control process to the image. As described in greater detail below, the automatic brightness control process may include identification of a region of interest in the image, and determination of a current brightness value for the identified region of interest to enable adjustment of one or more operating parameters of imaging system 108 to achieve a target brightness value for the identified region of interest. In some examples, image processor 118 may be or include a field-programmable gate array (FPGA), a digital signal processing (DSP) processor, a graphics processing unit (GPU), or the like.

Computing system 104 may further include an optional communication interface 120 for providing connectivity to network 140. Optional communication interface 120 may also provide connectivity to medical device 102 and/or display device(s) 106. In some examples, a communicative connection between computing system 104 and medical device 102 (or components thereof) and/or computing system 104 and display device(s) 106 may be at least partially supported via network 140.

Display device(s) 106 may be configured to display image data, including at least the image generated by computing system 104. In some examples, the image data may also include the image with a visual indicator of the region of interest identified as part of the automatic brightness control process. For example, the visual indicator may be overlaid at a location of the region of interest on the image. Display device(s) 106 may include one or more a combination of monitors, computing device screens, touch screen display devices, etc. In some examples, one or more of the display device(s) 106 may be a separate device from computing system 104 that is communicatively coupleable to computing system 104 via wired and/or wireless connections. In other examples, at least one of display device(s) 106 may be a display of computing system 104 itself.

In some examples, computing system 104 may generate, or may cause to be generated, one or more graphical user interfaces based on instructions or information stored in memory 114, instructions or information received from one or more optional server side system(s) 130, and/or the like and may cause the graphical user interfaces to be displayed via display device(s) 106. The graphical user interfaces may be, e.g., application interfaces or browser user interfaces and may include text, selection controls, and/or the like, in addition to the displayed image data. Display device(s) 106 may include a touch screen or a display with other input systems (e.g., a mouse, keyboard, voice, etc.) for an operator of computing system 104 to control functions of computing system 104, medical device 102 (or components thereof) via computing system 104, and/or display device(s) 106. As one example, the operator may select one or more of the control elements displayed on a graphical user interface of display device(s) 106 to manually adjust one or more operating parameters of imaging system 108 (e.g., based on operator preferences). The selection may be received by computing system 104 and cause corresponding signals to be transmitted from computing system 104 to imaging system 108 and/or specific components thereof.

One or more components of environment 100, such as medical device 102, computing system 104, and/or display device(s) 106, may be capable of network connectivity, and may communicate with one another over a wired or wireless network, such as network 140. Network 140 may be an electronic network. Network 140 may include one or more wired and/or wireless networks, such as a wide area network ("WAN"), a local area network ("LAN"), personal area network ("PAN"), a cellular network (e.g., a 3G network, a 4G network, a 5G network, etc.), or the like. In other examples, the components of environment 100 may communicate and/or connect to network 140 over universal serial bus (USB) or other similar local, low latency connections or direct wireless protocol. Components of environment 100 may be connected via network 140, using one or more standard communication protocols, such that the component may transmit and receive communications from each other across network 140.

In some examples, when one or more of the components of environment 100 are capable of connecting to network 140, environment 100 may also include one or more optional server side system(s) 130. Optional server side system(s) 130 may include one or more of remote image processing systems configured to perform at least a portion of the image processing, including but not limited, more resource intensive processes, such as machine learning processes (e.g., to conserve local resources of computing system 104 when network connectivity is available). Additionally or alternatively, optional server side system(s) 130 may include data storage systems for storing the image generated by computing system 104 (e.g., in response to receiving an action input from the operator to record or otherwise save the image). In some examples, at least one of the data storage systems may include a picture archiving and communication system (PACS) that stores the image, along with other types of imaging data from various imaging modalities (e.g., ultrasound, magnetic resonance, nuclear medicine imaging, positron emission tomography, computed tomography, mammograms, digital radiography, histopathology, etc.) associated with the patient.

Although various components in environment 100 are depicted as separate components in FIG. 1, it should be understood that a component or portion of a component in environment 100 may, in some embodiments, be integrated with or incorporated into one or more other components. For example, one of display device(s) 106 may be integrated with computing system 104 and/or computing system 104 may be integrated with medical device 102. In some embodiments, operations or aspects of one or more of the components discussed above may be distributed amongst one or more other components. Any suitable arrangement and/or integration of the various systems and devices of environment 100 may be used.

The specific examples included throughout the present disclosure implement an endoscopic imaging system configured to perform, in real or near real-time during a medical procedure, automatic brightness control processes based on an identified region of interest such that a brightness or illumination of the identified region of interest is optimized.

However, it should be understood that techniques according to this disclosure may be adapted to other medical imaging systems having varying types of imaging devices and light sources. It should also be understood that the examples above are illustrative only. The techniques and technologies of this disclosure may be adapted to any suitable activity.

Figure 2:
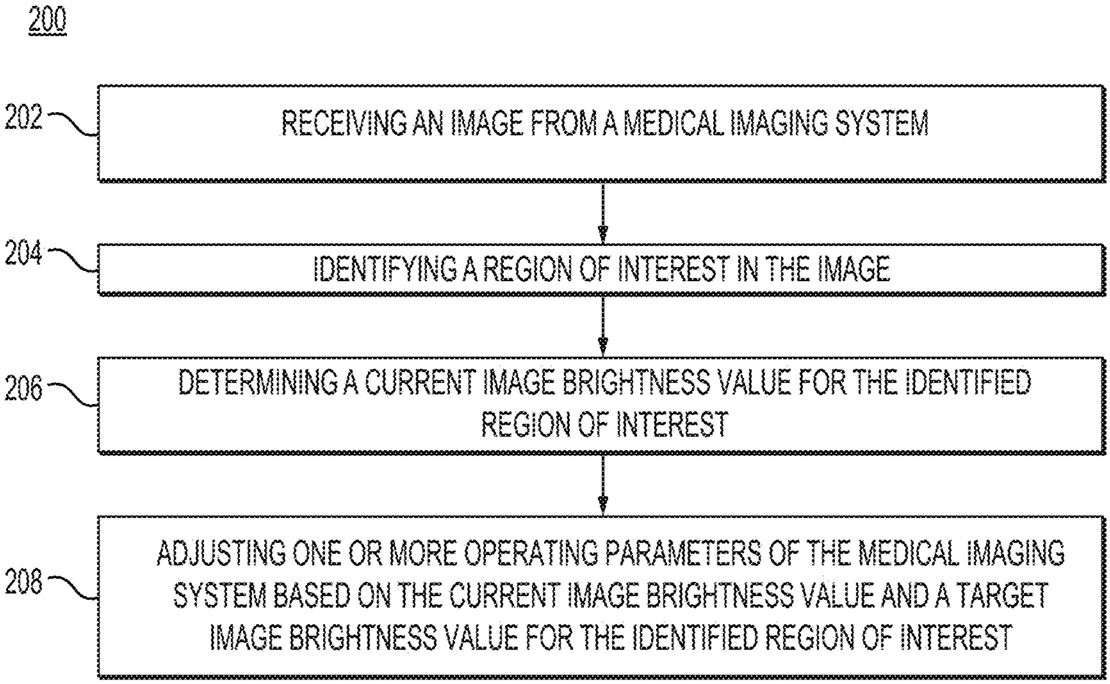
FIG. 2 depicts an example process for performing automatic brightness control based on an identified region of interest.

FIG. 2 depicts an example process 200 for performing automatic brightness control based on an identified region of interest. In some examples, one or more steps of process 200 may be performed by computing system 104. At step 202, the process 200 may include receiving an image from a medical imaging system, such as imaging system 108. For example, an image signal including raw image data captured by imaging device 110 as medical device 102 is positioned at a target site may be received and processed by image processor 118 to generate the image. The image may be provided to one or more of display device(s) 106 for display.

The image may be a color image, such as a red-green-blue (RGB) image, of the target site that is comprised of a plurality of pixels. The target site may include one or more objects or features of interest for visualization, such as polyps, lesions, and/or other objects, structures, or features indicative of abnormal tissue or foreign bodies.

At step 204, the process 200 may include identifying a region of interest in the image. The region of interest may include a subset of the pixels in the image that include the physical objects or features of interest in the target site for visualization in the image of the target site. The region of interest may be identified using one or more detection methods or techniques including, but not limited to, edge detection as described with reference to FIGS. 3A and 3B, color detection as described with reference to FIGS. 4A and 4B, or feature detection as described with reference to FIG. 5. In some examples, a visual indicator of the identified region of interest may be overlaid on the image and provided to one or more of display device(s) 106 for display.

At step 206, the process 200 may include determining a current image brightness value for the identified region of interest. For example, pixel values that represent an intensity or brightness of the subset of pixels included in the region of interest (e.g., pixel intensity values of the subset of pixels) may be averaged to determine the current image brightness value. For example, an average pixel intensity value for the subset of pixels may be the current image brightness value.

At step 208, the process 200 may include adjusting one or more parameters of imaging system 108 based on the current image brightness value and a target image brightness value for the identified region of interest. For example, a difference between the current image brightness value and the target brightness value may be determined. The difference may be utilized to adjust the one or more operating parameters such that the target brightness value is achieved for the identified region of interest. The target brightness value may be a predefined value for optimal (or otherwise improved) visualization. Specifically, the target brightness value may be a predefined percentage value of brightness on a scale of 0% (e.g., a fully black image) to 100% (e.g., a fully white image). As one non-limiting example, the target brightness value may be 40%+/−5% brightness. The target brightness value may be stored in memory 114 of computing system 104 and/or other data stores communicatively coupled to computing system 104 (e.g., data storage systems of optional server side system(s) 130) to enable retrieval of the target brightness value for use in the process 200.

In some examples, the target brightness value may be adjusted based on operator preferences. Continuing the example above, the target brightness value may be increased or decreased from the predefined percentage value of brightness to a higher or lower percentage value of brightness (e.g., may be increased to 50%+/−5%). The operator may interact with computing system 104 and/or display device(s) 106 (e.g., by providing input via one or more associated input systems or devices) to adjust the brightness value. In some examples, the adjusted brightness value may be saved and stored in association with the user in memory 114 and/or other data sources for subsequent retrieval and use.

One example operating parameter adjusted may be an intensity of light emitted by light source 112. To adjust the intensity, based on the current image brightness value, computing system 104 may control (e.g., may increase or decrease) an amount of current supplied to light source 112 to cause the intensity of light emitted by light source 112 to meet the target image brightness value. For example, a correlation between a value of current supplied to and light intensity emitted from light source 112 may be known based on information provided by a manufacturer of light source 112 and/or based on calibrations performed prior to distribution and/or use of medical device 102. Using the known correlation, computing system 104 may adjust the value of current supplied to light source 112 resulting in the current image brightness value to the value of current corresponding to a value of light intensity that meets the target image brightness value. The adjustment may be further dependent on a type of the anatomy at the target site. In some examples, computing system 104 may implement a Proportional Integral Derivative (PID) loop to control the intensity adjustment. Additionally or alternatively, dependent on a type of light source 112, computing system 104 may adjust one or more filters located between light source 112 and one or more fibers to adjust the intensity of light emitted, or reduce brightness of light source 112.

Another example operating parameter adjusted in step 208 may be a gain of imaging device 110. Gain adjustment may be one means of adjusting an apparent sensitivity of imaging device 110 to light. For example, the gain may represent a relationship between a number of electrons acquired on an image sensor of imaging device 110 and analog-to-digital units (ADUs) that are generated, representing the image signal. Increasing the gain amplifies the signal by increasing the ratio of ADUs to electrons acquired on the image sensor. Therefore, increasing gain may increase the apparent brightness of an image at a given exposure. Conversely, decreasing gain may decrease the apparent brightness. Based on the current image brightness value, computing system 104 may send signals to imaging device 110 to control (e.g., to increase or decrease) gain to achieve an apparent image brightness that meets the target image brightness value.

A further example operating parameter adjusted may be an exposure time of imaging device 110. The exposure time of imaging device 110, also referred to as shutter speed, may be a duration that the image sensor is exposed to the light. Increasing the duration may cause more light to be received by the sensor, resulting in increased pixel intensity and brightness of an image. Conversely, decreasing the duration may cause less light to be received by the sensor, resulting in decreased pixel intensity and brightness of the image. Based on the current image brightness value, computing system 104 may send signals to imaging device 110 to control (e.g., to increase or decrease) exposure time to achieve an image brightness that meets the target image brightness value.

The adjustment(s) performed at step 208 may optimize a brightness or illumination of the region of interest in subsequent images of the target site by, for example, optimizing raw image data captured by imaging device 110. In some examples, additional image processing techniques may be performed on the raw image data received to further enhance the brightness or illumination beyond what was achievable through the adjustments of the operating parameters of imaging system 108.

Accordingly, certain aspects may include performing automatic brightness control based on an identified region of interest. Process 200 described above is provided merely as an example, and may include additional, fewer, different, or differently arranged steps than depicted in FIG. 2.

Identification of Region of Interest Using Edge Detection Techniques

One or more regions in an image of an anatomical target site that include more detail relative to other regions of the image are candidate region(s) of interest, as a greater amount of detail may be indicative of abnormality (e.g., abnormal tissue, foreign body, etc.). Examples of a region including greater detail may include a region exposing underlying tissue vascularity, a region including differing textures in the tissue, a region including differing structures in the tissue (e.g., polyps, lesions, etc.), or a region including any other differing structures or appearances in the tissue indicative of a presence of an abnormality. Surrounding tissue (e.g., healthy walls of a body lumen) may be less detailed (e.g., smoother and/or lacking features) as compared to the region (s) of interest. Edge detection techniques may be used to identify such region(s) having more detail as region(s) of interest.

Figure 3A:
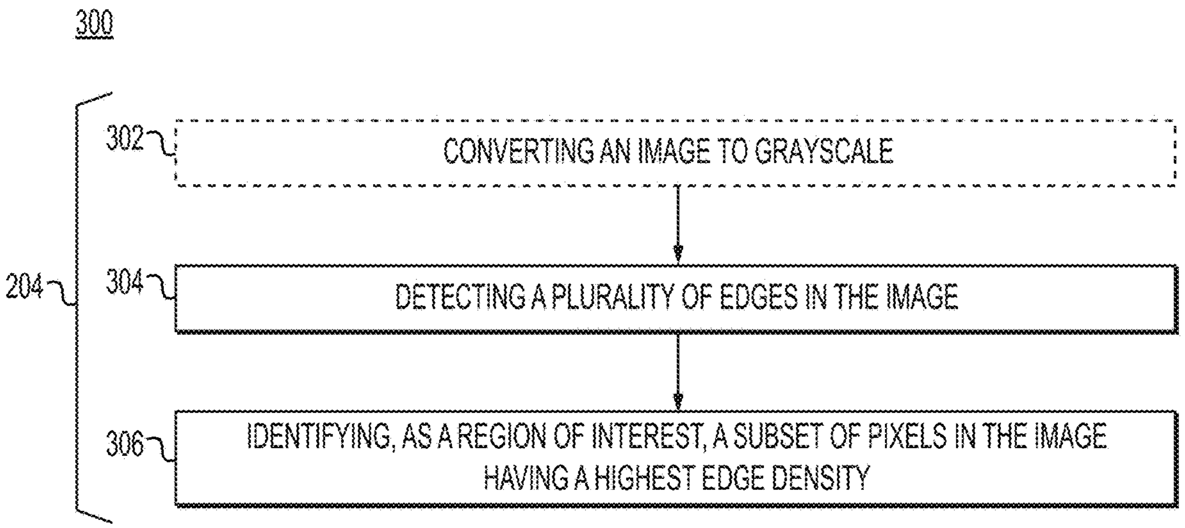
FIGS. 3A and 3B depict example processes for identifying a region of interest in an image using edge detection.
Figure 3B:
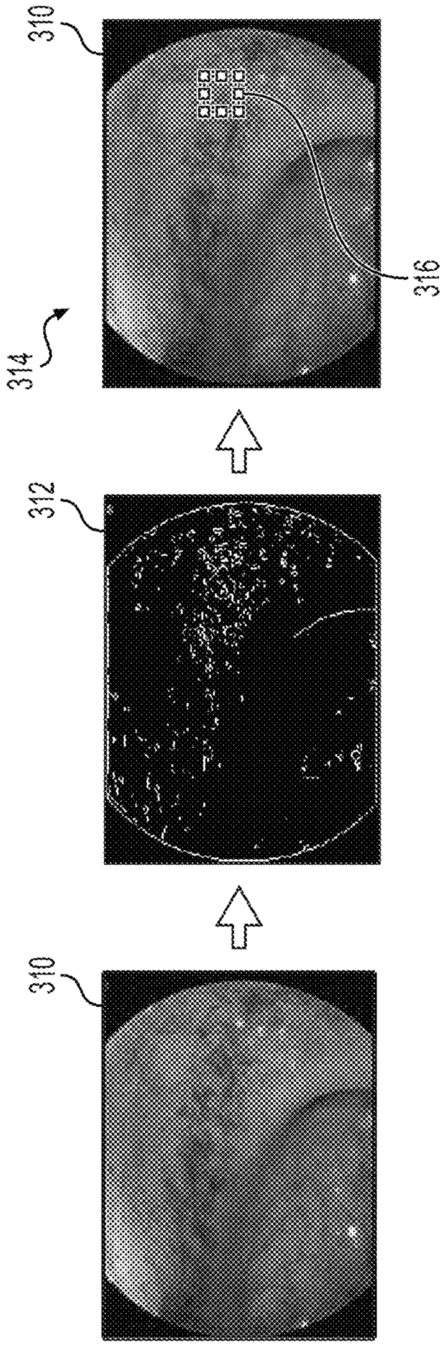

FIG. 3A depicts an example process 300 for identifying a region of interest in an image using edge detection. In some examples, one or more steps of process 300 may be performed by computing system 104. The process 300 may be used to perform at least part of step 204 of the process 200 described with reference to FIG. 2 to identify the region of interest. FIG. 3B depicts a conceptual diagram of images generated as part of process 300.

Referring concurrently to FIGS. 3A and 3B, at optional step 302, the process 300 may optionally include converting an image 310 captured by a medical imaging device to grayscale (e.g., to generate a grayscale image (not shown)). Image 310 may be the image received at step 202 of process 200 that is captured by imaging device 110. For example, image 310 may be a color image, such as a red-green-blue (RGB) image, that is comprised of a plurality of pixels. Image 310 may be converted using any known or future algorithm for converting a color image to a grayscale image. In some examples, raw image data received as part of the image signals captured by imaging device 110 may be converted directly to a grayscale image (e.g., as opposed to generating image 310 from the raw image data and then converting image 310 to grayscale). Image 310 may be converted to grayscale when a type of edge detection process applied at step 304, described below, is facilitated or otherwise enhanced by using a gray scale image (as opposed to a color image) as input to the edge detection process.

At step 304, the process 300 may include detecting a plurality of edges in image 310 (or in the grayscale image if the conversion at optional step 302 is performed). The edges may be identified using any known or future edge detection process or technique. In some examples, the edge detection may be performed on a specific color channel (e.g., one of red, green, or blue color channels) if, for example, the appearance of edges is driven by one of the color channels.

One example edge detection process that may be implemented is Sobel edge detection, which utilizes the Sobel operator or filter. When Sobel edge detection is implemented, image 310 may be converted to a grayscale image at optional step 302. Sobel edge detection techniques may include a measurement of pixel intensity values across the grayscale image to identify the edges based on variations in the pixel intensity values. For example, a 3×3 matrix (also known as the kernel) may be run over each of the pixels in the grayscale image. At every iteration, a change in gradient intensity values of the pixels that fall within the kernel may be measured in all directions. A greater change indicates a more significant edge at that pixel location. If the gradient intensity values measured in any of the directions exceed a predefined threshold, corresponding pixels may be set white. Remaining pixels not having gradient intensity values exceeding the predefined threshold may be set to black to generate a binary image, such as binary image 312. Other example edge detection processes may similarly generate a binary image comprising white and black pixels, where the white pixels represent detected edges, but may use varying techniques to do so based on a type of operator or filter utilized.

In some examples, the predefined threshold used as a basis for setting pixel values may be adjusted based on one or more factors. For example, an operator may manually adjust the threshold based on a type of anatomy and/or disease state being observed at the target site. Additionally or alternatively, the edge detection process may further include automatically adjusting the threshold. For example, the threshold may be automatically adjusted based on a percentage or ratio of white pixels to black pixels identified in binary image 312. For example, if binary image 312 has a large number of edges (e.g., includes mostly white pixels), the threshold may be automatically increased. Conversely, if binary image 312 has a low number of edges (e.g., includes mostly black pixels), the threshold may be automatically decreased.

At step 306, the process 300 may include identifying, as a region of interest 316, a subset of the pixels in image 310 having a highest edge density. To identify the subset of the pixels having the highest edge density, a sliding window of a predetermined size may be moved across binary image 312 to determine a number of white pixels that are representative of edges within each instance of the sliding window as it is moved. The sliding window may be of variable geometry. For example, the sliding window may be circular, elliptical, square, and/or rectangular, among other geometric shapes. As the sliding window is moved across binary image 312, a white pixel count of each subset of pixels forming a given instance of the sliding window may be determined. The subset of pixels forming the instance of the sliding window having a highest white pixel count (e.g., a highest density of edges) may be identified as region of interest 316.

In some examples, the predetermined size of the sliding window may be based on one or more physical objects and/or features in the target site attempting to be visualized and/or detected in the image of the target site. Additionally or alternatively, the predetermined size of the sliding window may be based on characteristics of the target site being imaged, such as whether the target site includes a flat wall or includes at least a portion of a lumen. Generally, the predetermined size of the sliding window needs to be large enough such that a brightness optimization based on a subset of pixels forming a given instance of the sliding window may provide a sufficient brightness or illumination across an entirety of the region of interest to enable appropriate visualization by the operator. On the other hand, the predetermined size of the sliding window should not be too large such that a subset of pixels forming a given instance of the sliding window encompasses a substantial portion of the image.

Once region of interest 316 is identified, a current image brightness value may be determined for the region of interest 316. The current image brightness value and a target image brightness value for the region of interest 316 may be used for adjusting one or more operating parameters of imaging system 108, as described in detail with reference to step 206 and step 208 of process 200. In some examples, a visual representation of identified region of interest 316 (e.g., visually represented by the instance of the sliding window having the highest density of edges) may be displayed or overlaid on image 310 to generate an augmented image 314. Augmented image 314 may be provided by computing system 104 to one or more of display device(s) 106 for display. While region of interest 316 is shown as a square in augmented image 314 of FIG. 3B, region of interest 316 may be other shapes dependent on a geometry of the sliding window. Additionally, in some examples, to prevent obstructing any pixels within region of interest 316, the visual representation of identified region of interest 316 may be at least slightly larger in size than the sliding window.

Accordingly, certain aspects may include performing edge detection processes for region of interest identification. Process 300 described above is provided merely as an example, and may include additional, fewer, different, or differently arranged steps than depicted in FIG. 3A.

Identification of Region of Interest Using Color Detection Techniques

Typically, healthy tissue will visually present as a similar (e.g., substantially uniform) color or shade in an image of the tissue. A polyp, precancerous lesion, or necrotic area of tissue, among other examples, may be a different color from surrounding healthy tissue. Therefore, detection of color or shade differences within an image of tissue (e.g., at a target site) may be used to identify a region of interest.

Figure 4A:
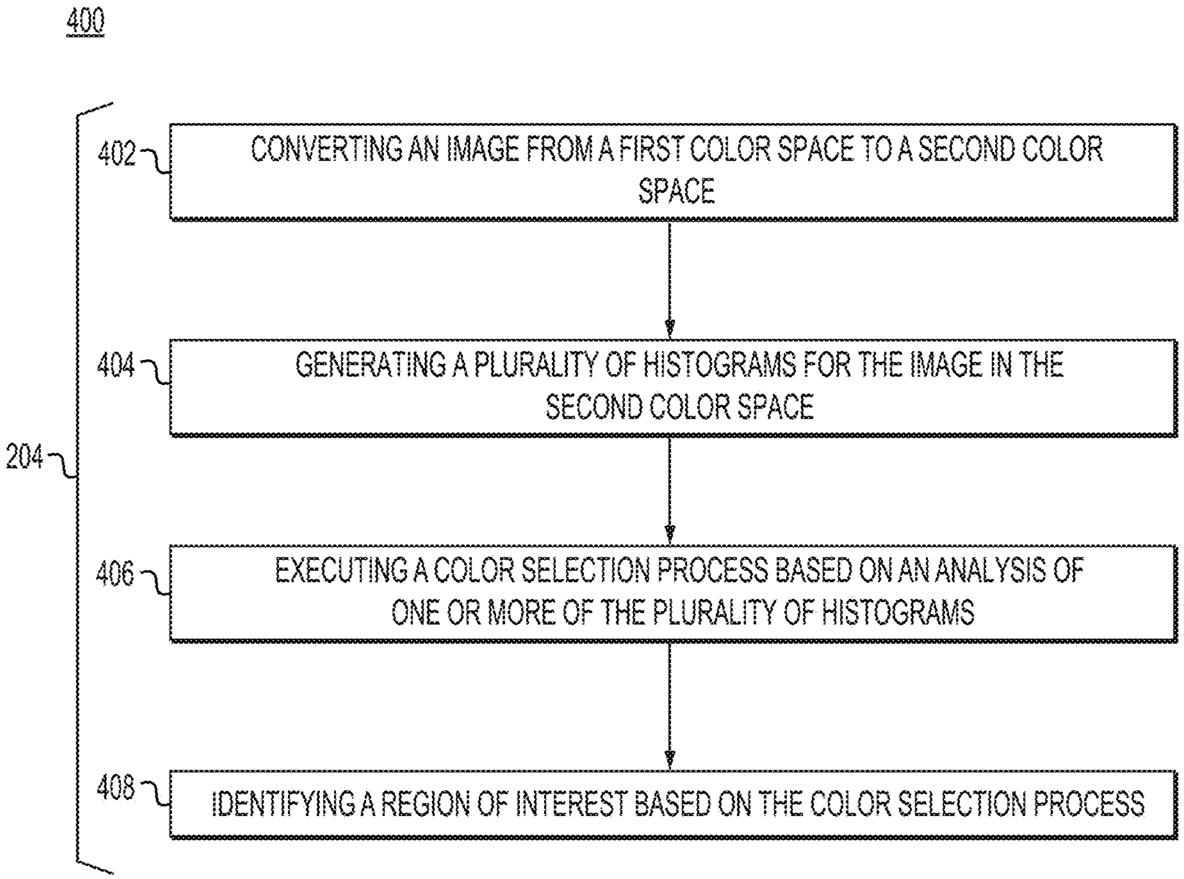
FIGS. 4A and 4B depict example processes for identifying a region of interest in an image using color detection.
Figure 4B:
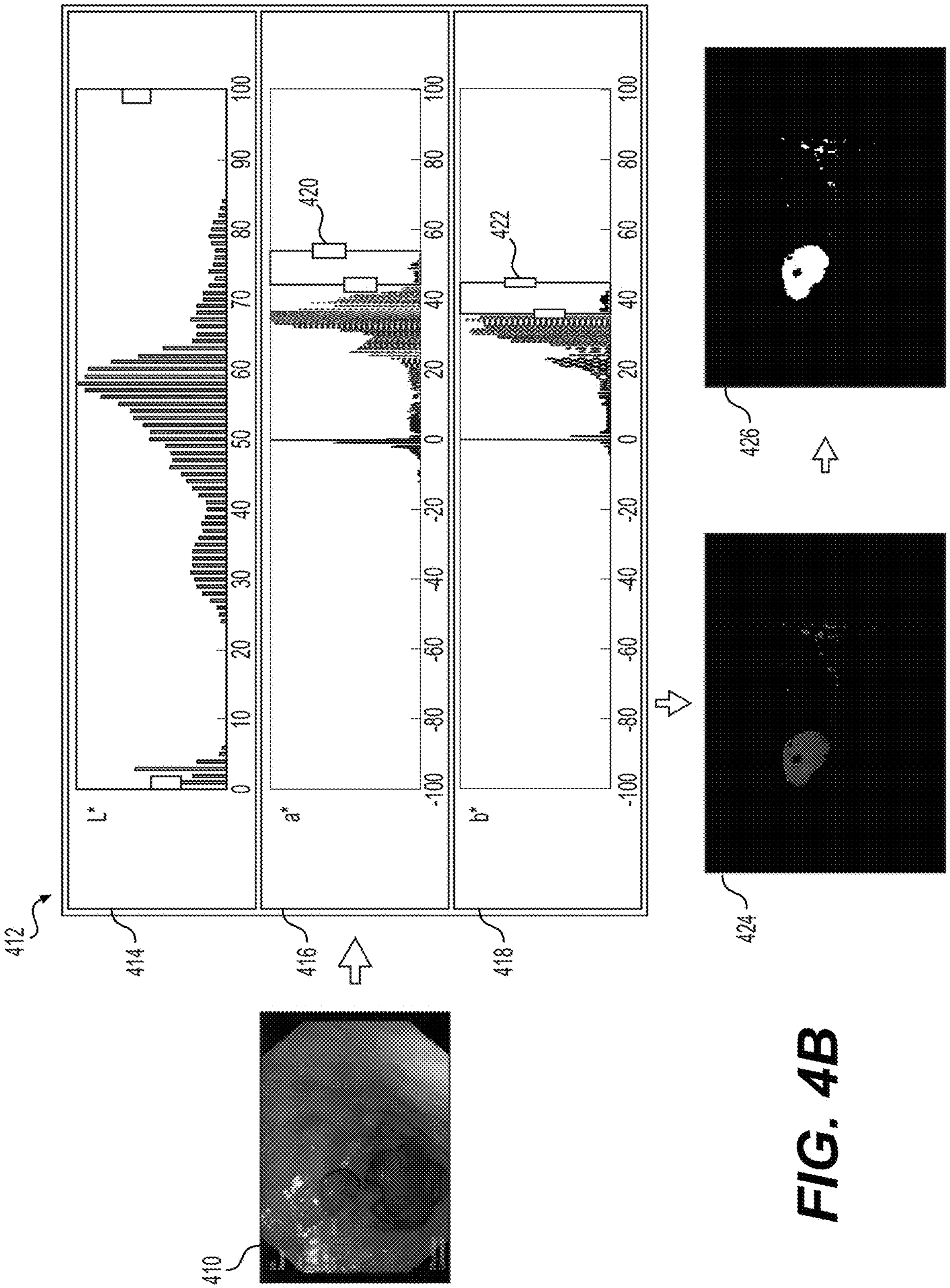

FIG. 4A depicts an example process 400 for identifying a region of interest in an image using color detection. In some examples, one or more steps of process 400 may be performed by computing system 104. The process 400 may be used to perform at least part of step 204 of the process 200 described with reference to FIG. 2 to identify the region of interest. FIG. 4B depicts a conceptual diagram of images and/or graphics generated as part of process 400.

Referring concurrently to FIGS. 4A and 4B, at step 402, the process 400 may include converting an image 410 from a first color space to a second color space. Image 410 may be the image captured by imaging device 110 received at step 202 of process 200. For example, image 410 may be a color image, such as a red-green-blue (RGB) image, that is comprised of a plurality of pixels. In such examples, the first color space may be a RGB color space having red, green, and blue channels, and image 410 may be converted to a second color space different from the RGB color space. The second color space may be a color space in which color properties of image 410 may be quantified to determine differences in shades of color (e.g., color shade differentiations). For example, the second color space may be the CIELAB color space comprising L*, a*, and b* channels. The L* channel may represent luminance (e.g., brightness), while the a* and b* channels represent chromaticity. Chromaticity may be an objective specification of a quality of color regardless of luminance. Specifically, the a* channel may represent chromaticity at a color position between red and green and the b* channel may represent chromaticity at a color position between yellow and blue.

At step 404, the process 400 may include generating a plurality of histograms 412 for the image in the second color space. A histogram may be generated for each of a plurality of channels in the second color space. Continuing with the example where the second color space is the CIELAB color space, histograms 412 may include a first histogram 414 for the L* channel, a second histogram 416 for the a* channel, and a third histogram 418 for the b* channel. First histogram 414 for the L* channel may represent a brightness distribution of image 410 that indicates a number of pixels (e.g., a pixel count) at each brightness intensity value on a scale of 0 to 100, for example. Second histogram 416 for the a* channel may represent a color distribution of image 410 that indicates a pixel count at each color position between red and green on an given scale. Third histogram 418 for the b* channel may represent a color distribution of image 410 that indicates a pixel count at each color position between yellow and blue on a given scale.

At step 406, the process 400 may include executing a color selection process based on an analysis of one or more of histograms 412. For example, a portion of histograms 412 representing color distributions, such as second histogram 416 and third histogram 418, may be analyzed to identify color shade differentiations across image 410, while excluding differences resulting from brightness (represented by L* channel). Further, one or more suspicious color areas in image 410 may be determined based on the analysis. For example, the suspicious color areas may be determined based on one or more detected deviations of the identified color shade differentiations from a typical pattern of color shade differentiations for a type of anatomy included in the image. As shown in second histogram 416 and third histogram 418, example deviations of the identified color shade differentiations from the typical pattern are visually highlighted by boxes 420, 422. A subset of the pixels contributing to the pixel counts at the color positions in the boxes 420, 422 may be identified as the suspicious color areas.

In some examples, the analysis of histograms 412 may include a comparison of histograms 412, and specifically a comparison of the color distribution representations depicted in second histogram 416 and third histogram 418, to one or more reference patterns of color shade differentiations for the type of anatomy to identify the deviations. The reference patterns may be generated based on an analysis of color distribution representations in a plurality of histograms generated for a* and b* channels in a plurality of images converted to the second color space. The images analyzed may depict healthy tissue of anatomy at the target site to enable identification of a typical pattern or range of how color is distributed across healthy tissue. A first reference pattern may be generated for the a* channel for comparison to second histogram 416. A second reference pattern may be generated for b* channel for comparison to third histogram 418.

In other examples, the analysis may include execution of a machine learning model trained to identify the deviations from one or more learned patterns of color shade differentiations for the type of anatomy. For example, and as described in more detail below, one or more of histograms 412 may be provided as input to the machine learning model to receive, as output, the deviations. The machine learning model may be executed by the computing system 104 (or one of optional server side system(s) 130 to conserve local computing resources).

In some examples, computing system 104 may one or more of generate, store, train, or use the machine learning model. The computing system 104 may include the machine learning model and/or instructions associated with the machine learning model, e.g., instructions for generating the machine learning model, training the machine learning model, using the machine learning model, etc. In other embodiments, a system or device other than computing system 104 may be used to generate and/or train the machine learning model. For example, such a system may include instructions for generating the machine learning model and the training data, and/or instructions for training the machine learning model. The trained machine learning model may then be provided to the computing system 104 for use.

To train the machine learning model, a plurality of training datasets may be obtained and processed to generate (e.g., build) the machine learning model. An exemplary training dataset may include a plurality of histograms generated for a plurality of images of a particular type of anatomy that is captured using a same modality of imaging device as imaging device 110 (e.g., image is an endoscopic image as opposed to an x-ray image) and has been converted from the first color space to the second color space. The histograms generated may be similar to histograms 412 generated at step 404. In some examples, when supervised or semi-supervised machine learning techniques are utilized, the exemplary training dataset may also include corresponding labels that indicate an actual subset of pixels in the images representing one or more deviations from a typical pattern of color distribution for the type of anatomy. In some examples, the model may be trained on color differences, rather than absolute colors. For example, the color differences (e.g., the color shade differentiations) from which the deviations are identified may be determined using Delta E measurements in the CIELAB color space. The model may be trained to identify subsets of pixels in images where the color differences (e.g., the Delta E) is abnormal or deviates from a typical pattern. The training datasets may be generated, received, or otherwise obtained from internal and/or external resources.

Generally, a model includes a set of variables, e.g., nodes, neurons, filters, etc., that are tuned, e.g., weighted or biased, to different values via the application of the training datasets. In some examples, the training process may employ supervised, unsupervised, semi-supervised, and/or reinforcement learning processes to train the model. In some examples, a portion of the training datasets may be withheld during training and/or used to validate the trained machine learning model.

When supervised learning processes are employed, the labels corresponding to images in the training datasets described above may facilitate the learning process by providing a ground truth. Training may proceed by feeding one or more histograms of a training dataset (e.g., a sample) from the training datasets into the model, the model having variables set at initialized values, e.g., at random, based on Gaussian noise, a pre-trained model, or the like. The model may output a subset of pixels for the sample predicted as deviating from a typical pattern of color distribution. The output may be compared with the corresponding label (e.g., the ground truth) indicating the actual subset of pixels representing the deviation(s) from the typical pattern of color distribution to determine an error, which may then be back-propagated through the model to adjust the values of the variables. This process may be repeated for a plurality of samples at least until a determined loss or error is below a predefined threshold.

For unsupervised learning processes, the training datasets may not include pre-assigned labels to aid the learning process. Rather, unsupervised learning processes may include clustering, classification, or the like to identify naturally occurring patterns in the training datasets. K-means clustering or K-Nearest Neighbors may also be used, which may be supervised or unsupervised. Combinations of K-Nearest Neighbors and an unsupervised cluster technique may also be used. For semi-supervised learning, a combination of training datasets with pre-assigned labels and training datasets without pre-assigned labels may be used to train the model.

When reinforcement learning is employed, an agent (e.g., an algorithm) may be trained to make a decision regarding the predicted subset of pixels for the sample from the training datasets through trial and error. For example, upon making a decision, the agent may then receive feedback (e.g., a positive reward if the predicted subset of pixels are indeed representative of deviation(s) from the typical pattern of color distribution), adjust its next decision to maximize the reward, and repeat until a loss function is optimized.

In some examples, the trained machine learning model may be generated and/or trained such that the model is commonly used or applied across images of varying anatomy types and/or across images of an anatomy type that include variable objects or features of interest therein. In other examples, separate, anatomy type-specific and/or object or feature type-specific trained machine learning models may be generated. For example, a first trained machine learning model may be generated for application to images of the esophagus, a second trained machine learning model may be generated for application to images of the stomach, and so on. Additionally or alternatively, a first set of trained machine learning models may be generated for application to images of the esophagus, where one of the models in the first set is applied to images of the esophagus including a polyp, another of the models in the first set is applied to images of the esophagus including a lesion, and so on.

Once trained, the machine learning model(s) may be stored (e.g., in memory 114 on computing system 104 and/or in one or more of the data storage systems associated with optional server side system(s) 130) and subsequently applied during a deployment phase. When a plurality of anatomy type-specific and/or object or feature type-specific machine learning models are generated and stored, the machine learning models may be stored in association with an identifier that indicates the specific anatomy type and/or object or feature type the machine learning model is trained for to facilitate the subsequent retrieval and application.

During the deployment phase, the trained machine learning model may receive input data. The input data may include one or more of histograms 412 generated at step 404, such as at least second histogram 416 and third histogram 418. The trained machine learning model may provide, as output data, a subset of pixels identified as deviations from a typical pattern of color distribution (e.g., suspicious color area(s)).

In some examples, the trained machine learning model may be re-trained or updated based on feedback received. For example, values or weights of one or more variables of the trained machine learning model may be adjusted to improve the accuracy of the trained machine learning model. The feedback may include an indication from the operator whether or not the subset of pixels identified as deviations are indeed the subset of pixels representing the region of interest. In some examples, when the subset of pixels identified is not accurate, the feedback may include a correct subset of pixels. The feedback may be used as a label to create new training datasets for use in retraining the trained machine learning model. In some examples, the trained machine learning model may be retrained after a predefined number of new training datasets have been received.

Returning to the color selection process of step 406, once one or more of histograms 412 have been analyzed to identify the color shade differentiations in image 410, and the suspicious color areas in the image have been determined based on a deviation of the identified color shade differentiations from the typical pattern, the color selection process may then be applied to image 410 based on the analysis. A masked image 424 may result. For example, to generate masked image 424, a mask may be applied to each pixel in image 410 that is not included in the identified suspicious color areas. Application of the mask to a given pixel may set the pixel to black. Each pixel to which the mask is applied may be referred to as a masked pixel. Remaining pixels of image 410 included in the identified suspicious color areas may be referred to as non-masked pixels.

At step 408, the process 400 may include identifying a region of interest based on the color selection process. In some examples, and as shown in FIG. 4B, a binary image 426 may be generated based on masked image 424 to facilitate the identifying of the region of interest. For example, pixel values of any non-masked pixels in masked image 424 (e.g., pixels included in the identified suspicious color areas) may be set to white, and the white pixels may be identified as the region of interest. In other examples, the non-masked pixels in masked image 424 may be directly identified as the region of interest.

Once the region of interest is identified, a current image brightness value may be determined for the region of interest. The current image brightness value and a target image brightness value for the region of interest may be used for adjusting the one or more operating parameters of imaging system 108, as described in detail with reference to step 206 and step 208 of process 200. In some examples, an augmented image including a visual indicator of the identified region of interest overlaid on image 410 may be generated using masked image 424 and/or binary image 426. The visual indicator may be an outline, shading, highlighting, and/or other similar visual emphasis of the non-masked pixels in masked image 424. In some examples, the visual indicator may also include a portion of masked pixels surrounding or neighboring the non-masked pixels to prevent obstruction of any of the non-masked pixels by the visual indicator. The augmented image may be provided by computing system 104 to one or more of display device(s) 106 for display.

Accordingly, certain aspects may include performing color detection processes for region of interest identification. Process 400 described above is provided merely as an example, and may include additional, fewer, different, or differently arranged steps than depicted in FIG. 4A.

Identification of Region of Interest Using Feature Detection Techniques

Prior to a patient undergoing a medical procedure using medical device 102, it is common for imaging of varying modalities (e.g., x-ray, computed tomography (CT), magnetic resonance imaging (MRI), positron emission tomography (PET), etc.) to be obtained for the patient and evaluated. From this pre-operative imaging and/or symptoms reported by the patient, a feature associated with an object or structure of interest at the target site for the medical procedure may be determined or at least inferred. For example, the target site may include a polyp or lesion, and a general shape of the polyp or lesion may be determined or inferred. As another example, the target site may include underlying tissue vascularity, and a grid-like pattern of the tissue vascularity may be determined or inferred. Therefore, detection of these features in an image of the target site captured during the medical procedure may be used to identify a region of interest.

Additionally, feature detection may be used as a default detection technique for identifying the region of interest (e.g., as opposed to using the above-described edge or color detection techniques) based on a type of the medical procedure being performed. For example, polyp and lesion feature detection may be the default detection technique applied to identify the region of interest when performing a cancer screening procedure.

Figure 5:
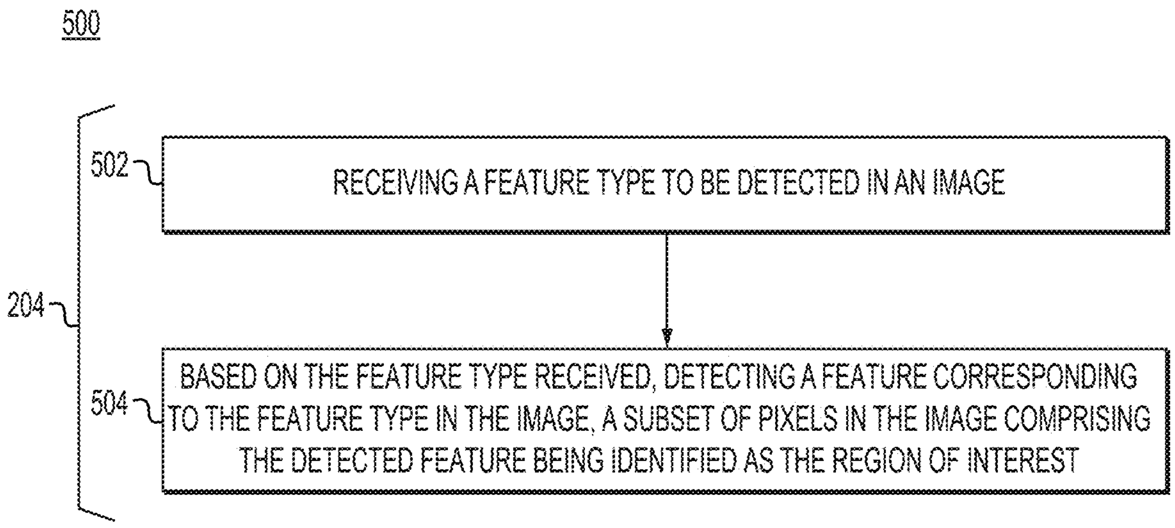
FIG. 5 depicts an example process for identifying a region of interest in an image using feature detection.

FIG. 5 depicts an example process 500 for identifying a region of interest in an image using feature detection. In some examples, one or more steps of process 500 may be performed by computing system 104. The process 500 may be used to perform at least part of step 204 of the process 200 described with reference to FIG. 2 to identify the region of interest.

At step 502, the process 500 may include receiving a feature type to be detected in an image. The image in which the feature type is to be detected may be the image of the target site captured by imaging device 110 that is received at step 202 of process 200. Example feature types received in step 502 may include a shape, a pattern, or other similar visual or appearance-based features expected to be present in association with an object or structure of interest at the target site. As one example, if the medical procedure is for biopsy or removal of a polyp, the feature type may be a circular or elliptical shape. As another example, if the medical procedure is being performed to observe underlying tissue vascularity at the target site, the feature type may be a grid-like pattern.

The feature type may be received as input to computing system 104. For example, the feature type may be received from input systems associated with computing system 104 and/or one or more of display device(s) 106. For example, the feature type may be manually input by an operator using the input systems by entering the feature type into a displayed text box, selecting a feature type from a displayed menu of feature type options, and/or other similar interactions with the computing system 104 and/or one or more of display device(s) 106. Additionally or alternatively, the operator may manually input the object or structure of interest, and computing system 104 may automatically select the feature type based on the object or structure of interest. For example, if the operator indicates a polyp as the object or structure of interest, a circular or elliptical shape may be automatically selected as the feature type.

In some examples, the feature type may be received prior to the medical procedure. For example, the feature type received may be based on information obtained from pre-operative imaging and/or symptoms reported by the patient. In other examples, the feature type may be received during the medical procedure once the target site is visualized. In further examples, the feature type may be received prior to the medical procedure and then subsequently adjusted during the procedure once the target site is visualized, if needed.

At step 504, the process 500 may include, based on the feature type received, detecting a feature corresponding to the feature type in the image. A subset of pixels in the image comprising the detected feature may be identified as the region of interest. The feature may be detected using any known or future feature detection process or technique. For example, the image and the feature type may be provided as input to a feature detection process, and each pixel in the image may be analyzed to determine whether a feature of the feature type is present at that pixel. Each pixel in which the feature of the feature type is determined to be present may be included within the subset of pixels identified as the region of interest. In some examples, when multiple feature types are received, step 504 may be performed iteratively for each feature type to identify one or more regions of interest corresponding to each feature type.

Once the region of interest is identified, a current image brightness value may be determined for the region of interest. The current image brightness value and a target image brightness value for the region of interest may be used for adjusting one or more operating parameters of imaging system 108, as described in detail with reference to step 206 and step 208 of process 200. In some examples, an augmented image including a visual indicator of the identified region of interest overlaid on the image may be generated. The visual indicator may be an outline, shading, highlighting, and/or other similar visual emphasis of the subset of pixels in which the feature of the feature type is determined to be present. In some examples, the visual indicator may also include a portion of pixels surrounding or neighboring the subset of pixels in which the feature of the feature type is determined to be present to prevent obstruction of any of the subset of pixels by the visual indicator. The augmented image may be provided by computing system 104 to one or more of display device(s) 106 for display.

Accordingly, certain aspects may include performing feature detection processes for region of interest identification. Process 500 described above is provided merely as an example, and may include additional, fewer, different, or differently arranged steps than depicted in FIG. 5.

Figure 6:
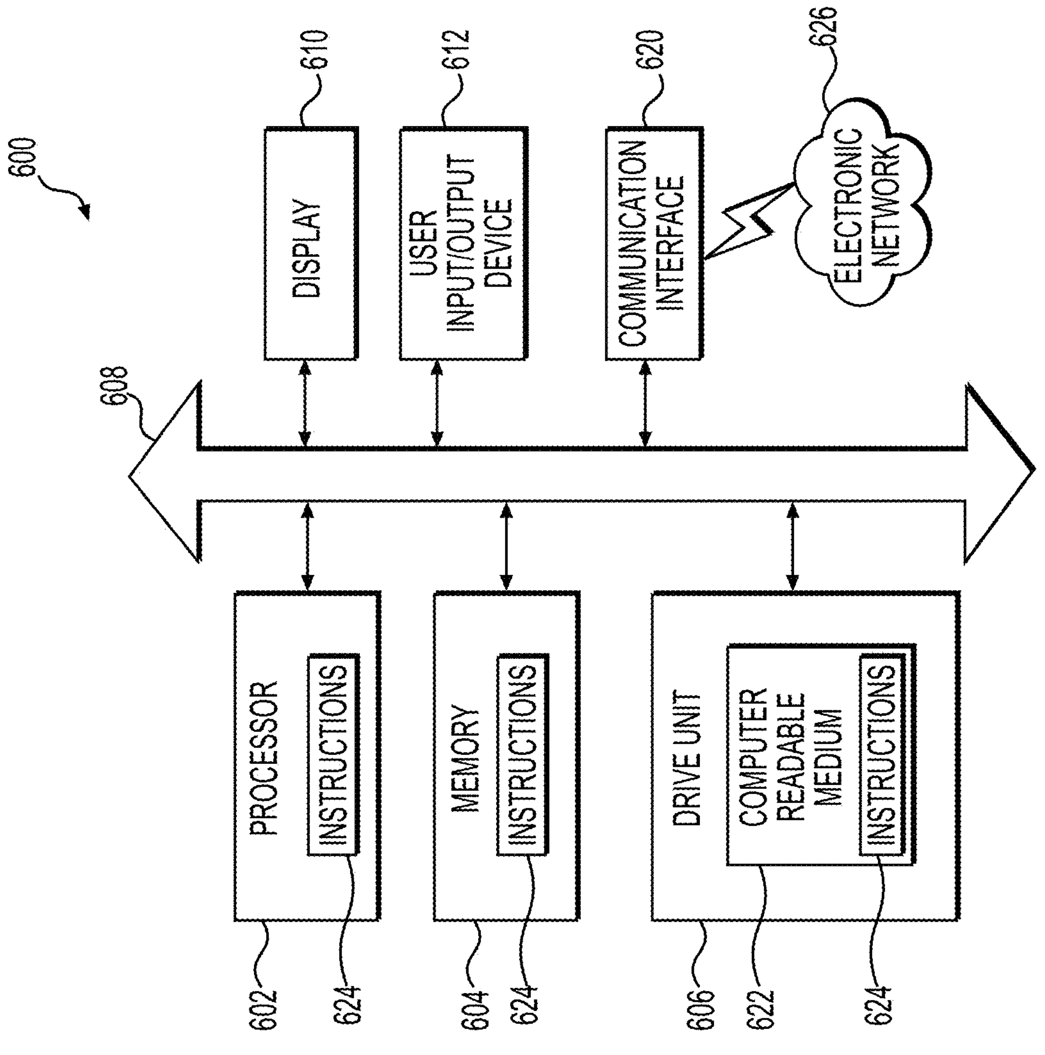
FIG. 6 depicts an example computing device.

FIG. 6 depicts an example of a computer 600. FIG. 6 is a simplified functional block diagram of computer 600 that may be configured as a device for executing processes, steps, or operations depicted in, or described with respect to, FIGS. 2-5 and, according to exemplary embodiments of the present disclosure. For example, computer 600 may be configured as one or more of medical device 102, computing system 104, display device(s) 106, optional server side system(s) 130, and/or another device or component according to exemplary embodiments of this disclosure. In various embodiments, any of the systems herein may be or include computer 600 including, e.g., a data communication interface 620 for packet data communication. Computer 600 may communicate with one or more other computers, for example, using an electronic network 626 (e.g., via data communication interface 620). Electronic network 626 may include a wired or wireless network, for example, similar to network 140 depicted in FIG. 1.

Computer 600 also may include a central processing unit ("CPU"), in the form of one or more processors 602, for executing program instructions 624. Program instructions 624 may include at least instructions for performing image processing, including region of interest-based automatic brightness control (e.g., if computer 600 is computing system 104).

Computer 600 may include an internal communication bus 608. Computer 600 may also include a drive unit 606 (such as read-only memory (ROM), hard disk drive (HDD), solid-state disk drive (SDD), etc.) that may store data on a computer readable medium 622 (e.g., a non-transitory computer readable medium), although computer 600 may receive programming and data via network communications. Computer 600 may also have a memory 604 (such as random-access memory (RAM)) storing instructions 624 for executing techniques presented herein. It is noted, however, that in some aspects, instructions 624 may be stored temporarily or permanently within other modules of computer 600 (e.g., processor 602 and/or computer readable medium 622). Computer 600 also may include user input and output devices 612 and/or a display 610 to connect with input and/or output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may, at times, be communicated through the Internet or various other telecommunication networks. Such communications, e.g., may enable loading of the software from one computer or processor into another. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While principles of this disclosure are described herein with the reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

I claim:

1. A method for performing automatic brightness control, the method comprising:

receiving an image of a target site from an imaging system of a medical device, wherein the image is in a first color space;

converting the image from the first color space to a second color space;

generating a plurality of histograms for the image in the second color space;

executing a color selection process, the color selection process including:

identifying color shade differentiations in the image based on an analysis of one or more of the plurality of histograms; and determining a suspicious color area in the image based on a deviation of the identified color shade differentiations from a pattern of color shade differentiations for a type of anatomy at the target site;

identifying a subset of pixels in the image comprising the suspicious color area as a region of interest in the image, the region of interest including a physical feature in the target site identified in the image;

determining a current image brightness value for the identified region of interest; and adjusting one or more operating parameters of the imaging system based on the current image brightness value and a target image brightness value.

2. The method of claim 1, wherein determining the current image brightness value based on the identified region of interest comprises:

determining an average pixel intensity value for the subset of pixels in the image comprising the suspicious color area, wherein the average pixel intensity value is the current image brightness value.

3. The method of claim 1, wherein the second color space includes a plurality of channels, and wherein generating the plurality of histograms comprises:

generating a histogram for each of the plurality of channels, wherein the one or more of the plurality of histograms analyzed represent color distributions in the image.

4. The method of claim 1, wherein determining the suspicious color area comprises:

comparing the one or more of the plurality of histograms to one or more reference patterns of color shade differentiations for the type of anatomy to identify the deviation.

5. The method of claim 1, wherein determining the suspicious color area comprises:

providing the one or more of the plurality of histograms as input to a machine learning model trained to identify the deviation from one or more learned patterns of color shade differentiations for the type of anatomy.

6. The method of claim 1, wherein executing the color selection process further includes:

applying a mask to each pixel in the image that is not included in the suspicious color area to generate a masked image.

7. The method of claim 6, further comprising:

generating a binary image based on the masked image to facilitate the identifying of the region of interest.

8. The method of claim 1, wherein the imaging system includes a light source configured to illuminate the target site, and adjusting the one or more operating parameters of the imaging system comprises:

adjusting an intensity of light emitted by the light source to illuminate the target site, wherein the intensity of light is adjusted by controlling an amount of current supplied to the light source.

9. The method of claim 1, wherein the imaging system includes an imaging device configured to capture the image, and adjusting the one or more operating parameters of the imaging system comprises:

adjusting one or more of a gain or an exposure time of the imaging device.

10. A computing system for performing automatic brightness control, the computing system comprising:

at least one memory storing instructions; and at least one processor coupled to the at least one memory and configured to execute the instructions to perform operations, including:

receiving, from a medical imaging system including an imaging device and a light source, an image of a target site captured by the imaging device as the light source is illuminating the target site, the image including a plurality of pixels;

converting the image from a first color space to a second color space;

generating a plurality of histograms for the image in the second color space;

identifying color shade differentiations in the image based on an analysis of the one or more of the plurality of histograms;

determining a suspicious color area in the image based on a deviation of the identified color shade differentiations from a pattern of color shade differentiations for a type of anatomy at the target site;

identifying a subset of the plurality of pixels in the image comprising the suspicious color area as a region of interest in the image, the subset of the plurality of pixels including a physical feature in the target site detected in the image;

determining a current image brightness value based on an average pixel intensity value for the subset of the plurality of pixels; and based on the current image brightness value, adjusting one or more operating parameters of one or more of the light source or the imaging device to achieve a target image brightness value for the subset of the plurality of pixels identified as the region of interest.

11. A medical imaging system comprising:

a medical device including an imaging device configured to capture an image of a target site in a first color space and a light source configured to illuminate the target site as the image is captured; and a computing device communicatively coupled to the medical device, the computing device comprising:

at least one memory storing instructions; and at least one processor coupled to the at least one memory and configured to execute the instructions to perform operations, including:

receiving the image from the medical device;

identifying a region of interest in the image including a physical feature in the target site detected in the image, the region of interest identified using color detection, the color detection including:

converting the image from the first color space to a second color space;

generating a plurality of histograms for the image in the second color space;

identifying color shade differentiations in the image based on an analysis of the one or more of the plurality of histograms; and determining a suspicious color area in the image based on a deviation of the identified color shade differentiations from a pattern of color shade differentiations for a type of anatomy at the target site, wherein a subset of pixels in the image comprising the suspicious color area is identified as the region of interest;

determining a current image brightness value for the identified region of interest; and adjusting one or more operating parameters of one or more of the light source or the imaging device based on the current image brightness value and a target brightness value for the identified region of interest to optimize a brightness of the region of interest in subsequent images of the target site captured by the imaging device.

12. The method of claim 1, wherein the one or more of the plurality of histograms analyzed include a portion of the plurality of histograms representing a color distribution of the image.

13. The method of claim 1, wherein the first color space is a red-green-blue (RGB) color space and the second color space is a CIELAB color space.

14. The method of claim 12, wherein the second color space includes three channels, and wherein generating the plurality of histograms comprises:

generating a histogram for each of the three channels, wherein a first histogram for a first channel represents a brightness distribution of the image, a second histogram for a second channel represents a first color distribution of the image, and a third histogram for a third channel represents a second color distribution of the image.

15. The method of claim 14, wherein the first color distribution indicates a pixel count at each color position between red and green, and the second color distribution indicates a pixel count at each color position between yellow and blue.

16. The method of claim 14, wherein identifying the color shade differentiations in the image based on the analysis of the one or more of the plurality of histograms comprises:

identifying the color shade differentiations in the image based on the analysis of the second histogram and the third histogram.

* * * * *